US007857795B2

(12) United States Patent
Perrin et al.

(10) Patent No.: US 7,857,795 B2
(45) Date of Patent: Dec. 28, 2010

(54) EYEWASH SYSTEM

(75) Inventors: Timothy E. Perrin, Hartford, WI (US); Gerard Val Madritsch, Milwaukee, WI (US); Theodore E. Dhein, Sussex, WI (US); Jeffery S. Jaworski, Sussex, WI (US)

(73) Assignee: Bradley Fixtures Corporation, Menomonee Falls, WI (US)

( * ) Notice: Subject to any disclaimer, the term of this patent is extended or adjusted under 35 U.S.C. 154(b) by 495 days.

(21) Appl. No.: 11/978,520

(22) Filed: Oct. 29, 2007

(65) Prior Publication Data

US 2008/0119799 A1 May 22, 2008

Related U.S. Application Data

(60) Provisional application No. 60/855,272, filed on Oct. 30, 2006.

(51) Int. Cl.
*A61M 35/00* (2006.01)
*A61H 35/02* (2006.01)

(52) U.S. Cl. .......................................... 604/294; 4/620

(58) Field of Classification Search ......... 604/294–298; 4/619, 620

See application file for complete search history.

(56) References Cited

U.S. PATENT DOCUMENTS 1,879,344 A 9/1932 Lawler
2,317,717 A 4/1943 Bauman
2,792,847 A 5/1957 Spencer
2,910,064 A * 10/1959 Brangaitis .................. 604/301
3,061,195 A 10/1962 Bowman
3,782,412 A 1/1974 Darash
3,871,554 A * 3/1975 Huck .......................... 222/96
3,976,072 A * 8/1976 Walker ....................... 424/429
4,012,798 A 3/1977 Liautaud
4,195,656 A 4/1980 Kanerva et al.
4,259,953 A * 4/1981 Shaw ......................... 604/302
4,363,146 A 12/1982 Liautaud
4,862,913 A 9/1989 Wildfang
4,881,283 A 11/1989 Liautaud
4,939,800 A 7/1990 Fiorentino et al.
5,008,963 A 4/1991 Stein
5,102,010 A 4/1992 Osgar et al.
5,157,798 A * 10/1992 Van Kammen ................. 4/620
5,171,307 A 12/1992 Sanning
5,216,765 A 6/1993 Paterson et al.
5,320,615 A * 6/1994 Van Keuren ................ 604/297

(Continued)

OTHER PUBLICATIONS

Bradley Corporation Emergency Fixtures Sep. 2006.*

(Continued)

*Primary Examiner*—Tatyana Zalukaeva
*Assistant Examiner*—Paula L Craig
(74) *Attorney, Agent, or Firm*—Foley & Lardner LLP

(57) ABSTRACT

An eyewash system for dispensing an eyewash fluid is disclosed. The eyewash system comprises a dispensing assembly having an inlet portion, an outlet portion, and a valve configurable between an open position and a closed position. The eyewash system also comprises a first tank in communication with the inlet portion of the dispensing assembly, and a second tank in communication with the inlet portion of the dispensing assembly. The outlet portion is configured to dispense eyewash fluid from both the first tank and the second tank when the valve is configured in the open position.

18 Claims, 11 Drawing Sheets

U.S. PATENT DOCUMENTS

| | | | | | |
|---|---|---|---|---|---|
| 5,381,567 | A | | 1/1995 | Tanner et al. | |
| 5,566,406 | A | | 10/1996 | Demeny et al. | |
| 5,638,989 | A | * | 6/1997 | Ophardt et al. | 222/105 |
| 5,695,124 | A | * | 12/1997 | Demeny et al. | 239/327 |
| 6,070,279 | A | * | 6/2000 | Lundstedt | 4/620 |
| 6,158,486 | A | | 12/2000 | Olson et al. | |
| D438,983 | S | | 3/2001 | Stein | |
| 6,280,408 | B1 | | 8/2001 | Sipin | |
| 6,296,626 | B1 | | 10/2001 | Stein | |
| 6,398,766 | B1 | * | 6/2002 | Branch | 604/302 |
| 6,543,478 | B2 | | 4/2003 | Kline | |
| 6,610,036 | B2 | | 8/2003 | Branch et al. | |
| 6,837,267 | B2 | | 1/2005 | Weis et al. | |
| 6,976,279 | B1 | * | 12/2005 | Berke et al. | 4/620 |
| 7,011,652 | B1 | * | 3/2006 | Berke et al. | 604/300 |
| D529,185 | S | | 9/2006 | Zhou | |
| 7,143,784 | B2 | | 12/2006 | Fangmeier et al. | |
| 7,254,848 | B2 | | 8/2007 | Johnson et al. | |
| 7,278,177 | B1 | | 10/2007 | Duffie | |
| 2002/0107492 | A1 | * | 8/2002 | Brach et al. | 604/296 |
| 2005/0217019 | A1 | * | 10/2005 | Johnson et al. | 4/620 |
| 2007/0089233 | A1 | * | 4/2007 | Smith et al. | 4/620 |
| 2007/0106230 | A1 | * | 5/2007 | Kelloway | 604/258 |
| 2009/0007327 | A1 | | 1/2009 | Johnson et al. | |

OTHER PUBLICATIONS

Bradley Corporation, Installation S19-921, S19-921H, S19-921HR, Sep. 12, 2007; 19 pages.

Bradley Corporation, Plumbing Fixtures Technical Data, On-Site® Gravity-Fed Eyewash, Model S19-921, S19-921H and S19-899, Mar. 20, 2007; 2 pages.

Neoperl, NV25 Check Valve Insert, bearing a designation "06/06"; 1 page.

International Search Report and Written Opinion of the International Searching Authority for International Application No. PCT/US2007/082865; mailed Mar. 4, 2008; 12 pages.

* cited by examiner

FIG. 9
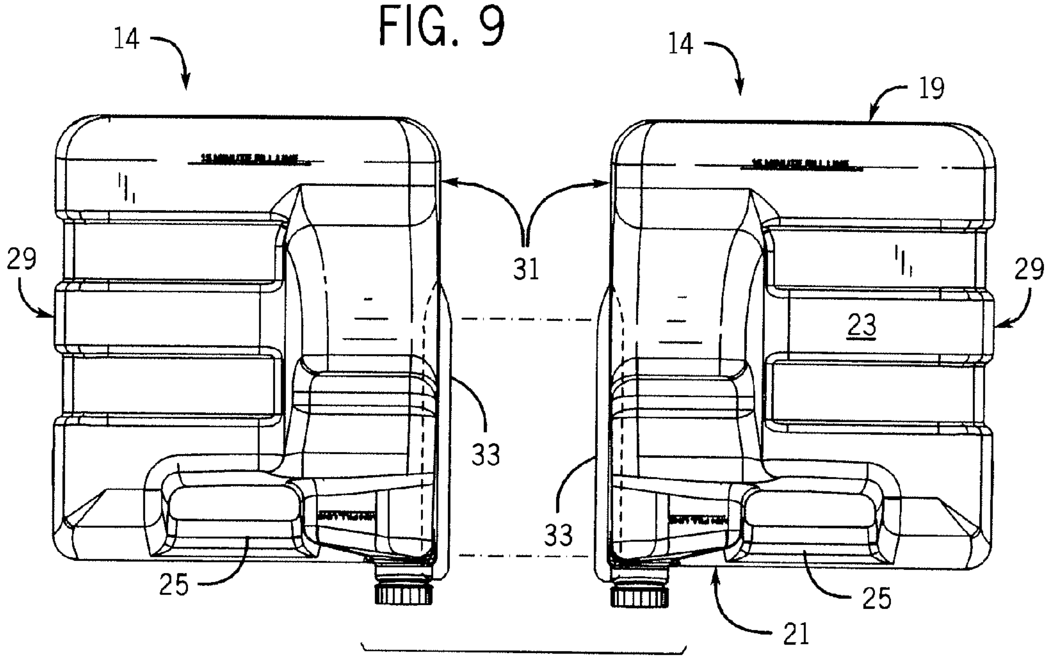
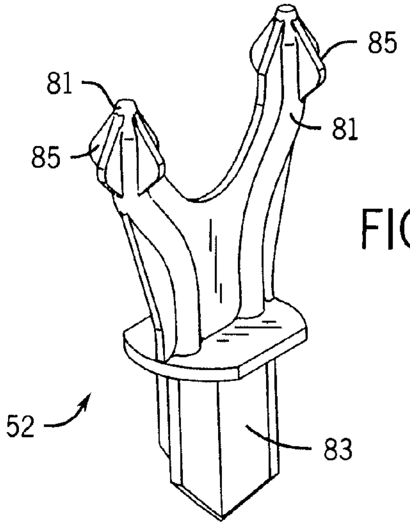
FIG. 10
FIG. 11
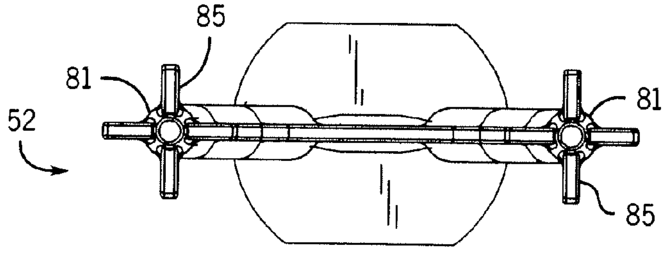

EYEWASH SYSTEM

CROSS-REFERENCE TO RELATED APPLICATIONS

The present application claims priority under 35 U.S.C. §119 from U.S. Provisional Patent Application No. 60/855,272 titled "EYEWASH SYSTEM" filed Oct. 30, 2006, the full disclosure of which is hereby incorporated herein by reference.

BACKGROUND

The present invention relates to an eyewash station or system. More particularly, the present invention relates to an eyewash system having two or more tanks. Still more particularly, the present invention relates to a portable eyewash system having a two or more tanks with check valves.

It is generally known to provide an eyewash system configured for flooding or rinsing of one or both of the eyes of a person (e.g., a worker or other user) with water or a fluid solution in order to remove, dilute, or neutralize a contaminant or other foreign material. Such known eyewash systems often include a single tank of fluid that is elevated with respect to a flow outlet configured to spray a fluid stream into the user's eyes. The tank, which must be refilled after the system has been used or on a periodic maintenance basis. The weight of such a single tank filled with eyewash fluid can be unwieldy if not impossible to lift for some people, and otherwise difficult to refill without spillage and align during installation.

Accordingly, it would be advantageous for an eyewash system to include a removable tank configured for convenient installation. It would also be advantageous for an eyewash system to be configured for ease of installation and maintenance, for example wherein a user does not have to lift and align a heavy tank of eyewash fluid. To provide an inexpensive, reliable, and widely adaptable eyewash system that avoids the above-referenced and other problems would represent a significant advance in the art.

SUMMARY

One embodiment of the invention relates to an eyewash system for dispensing an eyewash fluid. The eyewash system comprises a dispensing assembly having an inlet portion, an outlet portion, and a valve configurable between an open position and a closed position; a first tank in communication with the inlet portion of the dispensing assembly; and a second tank in communication with the inlet portion of the dispensing assembly. The outlet portion is configured to dispense eyewash fluid from both the first tank and the second tank when the valve is configured in the open position.

Another embodiment of the invention relates to an eyewash system for dispensing a fluid. The system comprises a first tank having a first check valve configurable between a first position; a second tank having a second check valve configurable between a first position; and a dispensing assembly having an inlet portion, an outlet portion, and a valve configurable between an open position and a closed position. Fluid is inhibited from flowing from the first tank and a second position wherein fluid is permitted to flow from the first tank. Fluid is inhibited from flowing from the second tank and a second position wherein fluid is permitted to flow from the second tank. The inlet portion of the dispensing assembly engages the first tank to configure the first check valve in the second position and engages the second tank to configure the second check valve in the second position so that the outlet portion dispenses eyewash fluid from both the first tank and the second tank when the valve is configured in the open position.

Another embodiment of the invention relates to an eyewash system for dispensing a fluid. The system comprises a dispensing assembly having an inlet portion, an outlet portion, and a valve configurable between an open position and a closed position; a first tank in communication with the inlet portion of the dispensing assembly; a second tank in communication with the inlet portion of the dispensing assembly; a first check valve coupled to the first tank and configurable between a first position; a second check valve coupled to the second tank and configurable between a first position; a first member extending from the dispensing assembly to configure the first check valve in the second position; and a second member extending from the dispensing assembly to configure the second check valve in the second position. Fluid is inhibited from flowing through the first check valve and a second position wherein fluid is permitted to flow through the first check valve. Fluid is inhibited from flowing through the second check valve and a second position wherein fluid is permitted to flow through the second check valve. The outlet portion is configured to simultaneously dispense eyewash fluid from both the first tank and the second tank when the valve is configured in the open position.

Another embodiment of the invention relates to a tank for retaining and dispensing the eyewash fluid for an eyewash system. The tank comprises a body defining an interior to retain the eyewash fluid and having an outlet through which the eyewash fluid flows out of the body; and a check valve coupled to the body at the outlet and configurable between a first position wherein fluid is inhibited from flowing through the check valve and a second position wherein fluid is permitted to flow through the check valve.

The present invention further relates to various features and combinations of features shown and described in the disclosed embodiments. Other ways in which the objects and features of the disclosed embodiments are accomplished will be described in the following specification or will become apparent to those skilled in the art after they have read this specification. Such other ways are deemed to fall within the scope of the disclosed embodiments if they fall within the scope of the claims which follow.

BRIEF DESCRIPTION OF THE DRAWINGS

FIG. 9 is an exploded front view of a pair of eyewash fluid tanks.

FIG. 10 is a perspective view of an activator that engages check valves on the pair of eyewash fluid tanks.

FIG. 11 is a top view of the activator of FIG. 10.

DETAILED DESCRIPTION OF THE PREFERRED AND EXEMPLARY EMBODIMENTS

Figure 1:
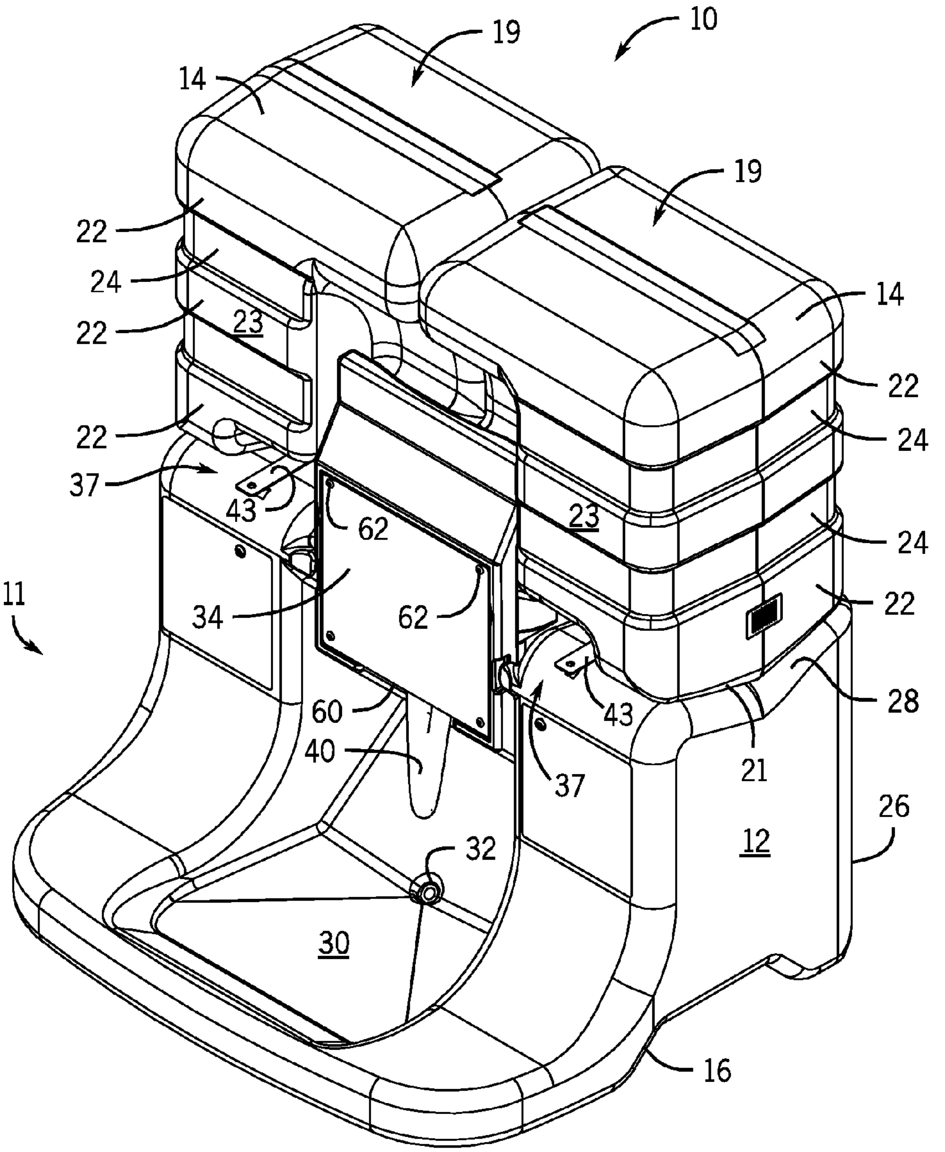
FIG. 1 is a perspective view of an eyewash system in a non-dispensing configuration.
Figure 2:
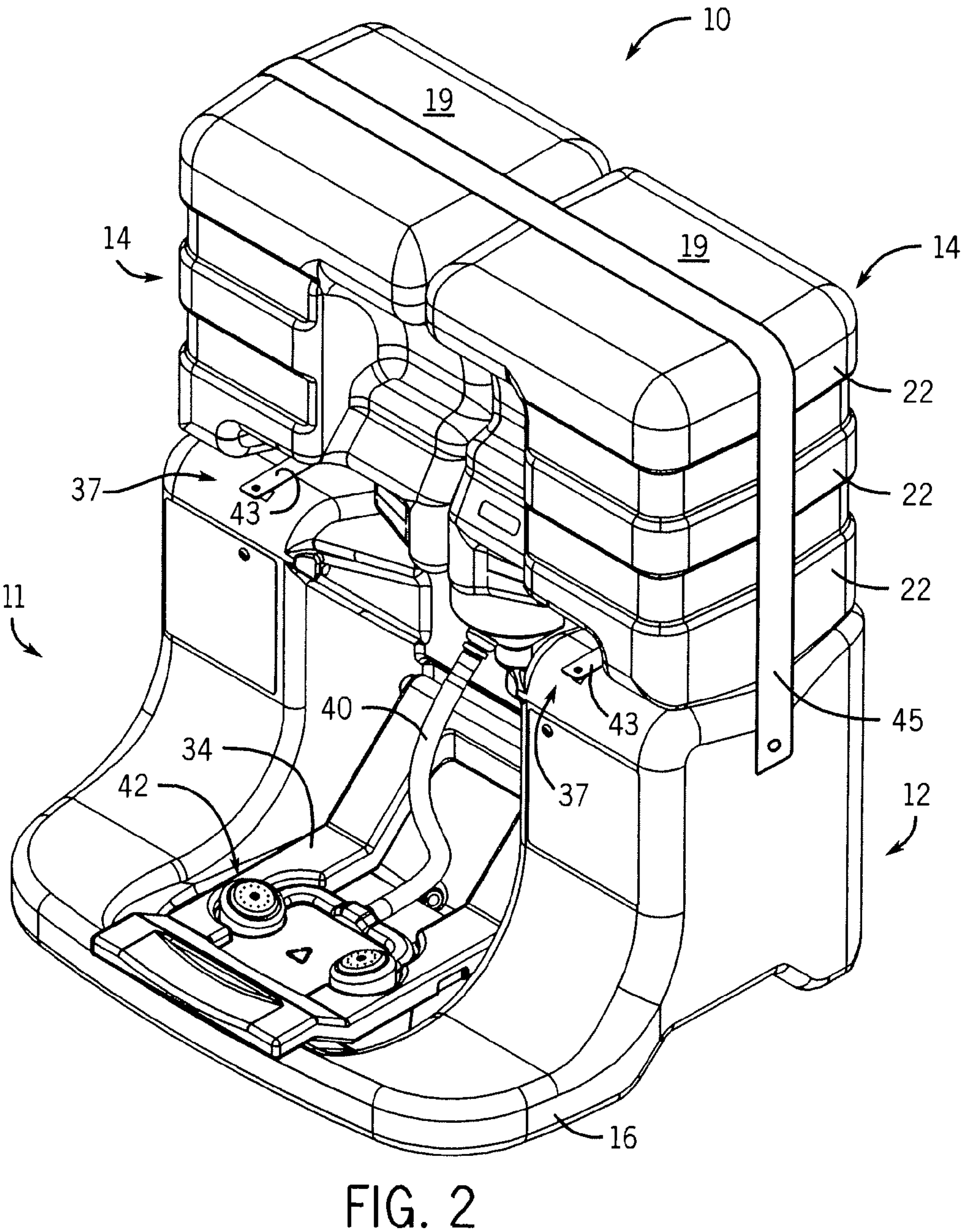
FIG. 2 is a perspective view of the eyewash system of FIG. 1 in a dispensing configuration.
Figure 3:
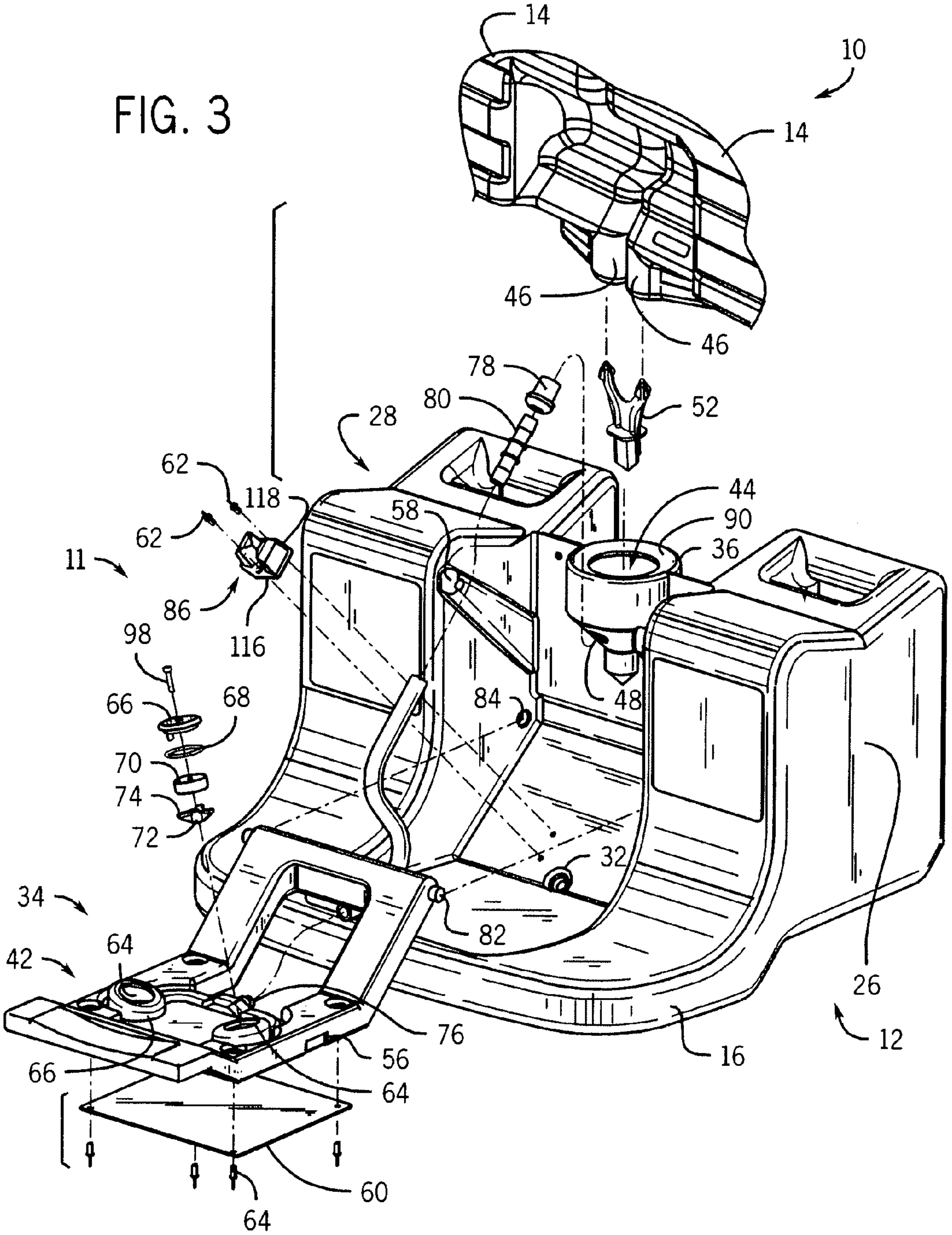
FIG. 3 is a fragmentary exploded view perspective of the eyewash system of FIG. 2.
Figure 4:
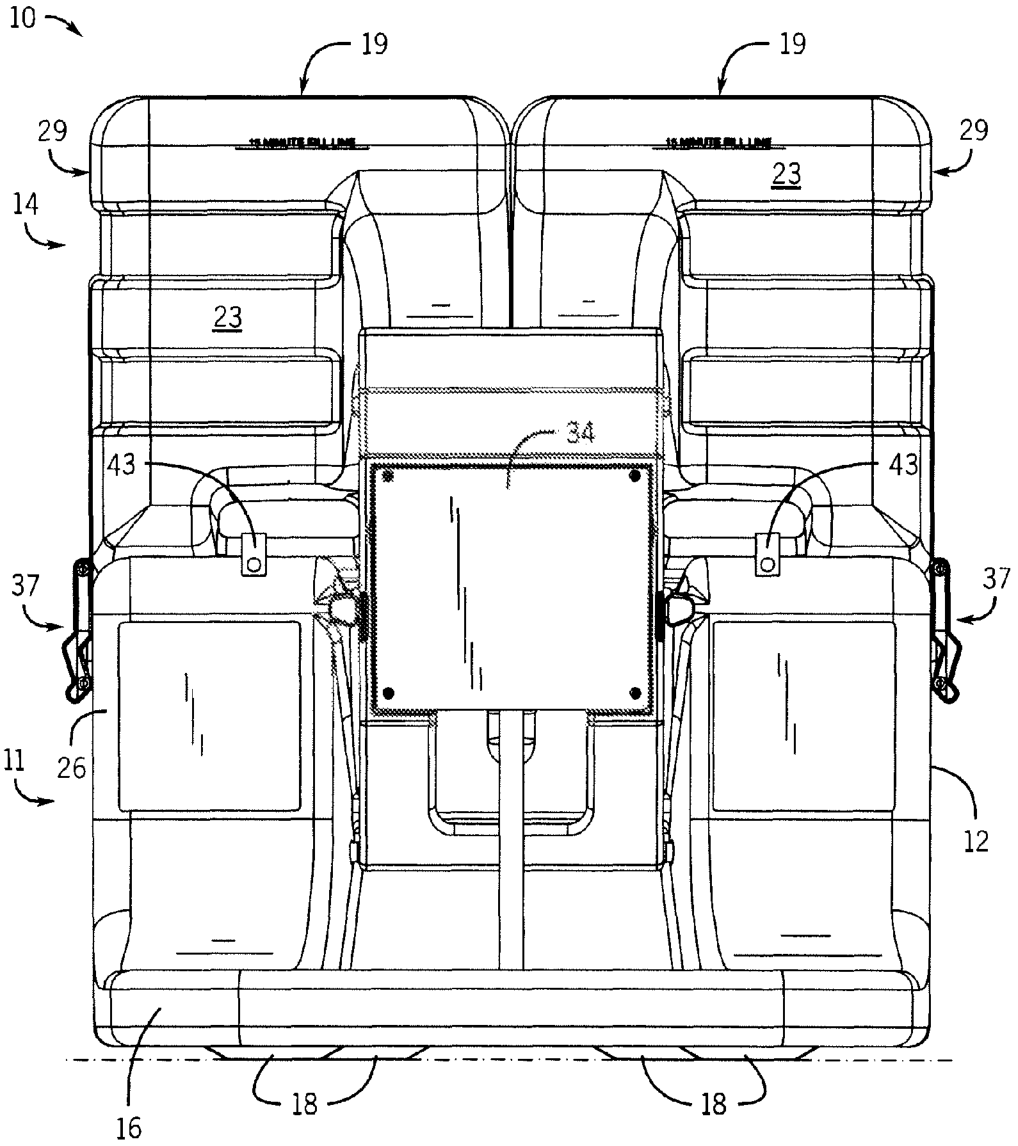
FIG. 4 is a front view of the eyewash system of FIG. 1.
Figure 5:
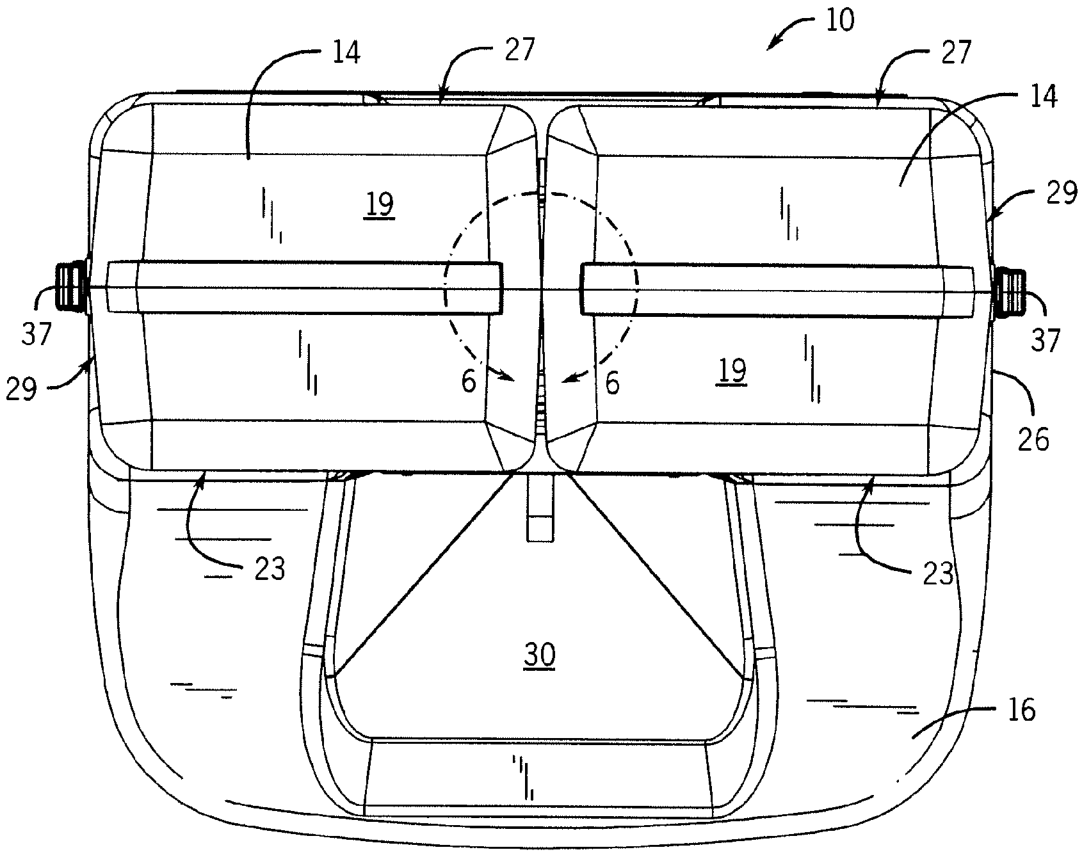
FIG. 5 is a top view of the eyewash system of FIG. 1.
Figure 6:
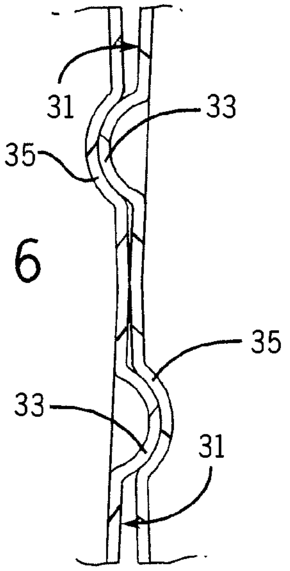
FIG. 6 is a section view of the interface of the eyewash fluid tanks of FIG. 5.
Figure 7:
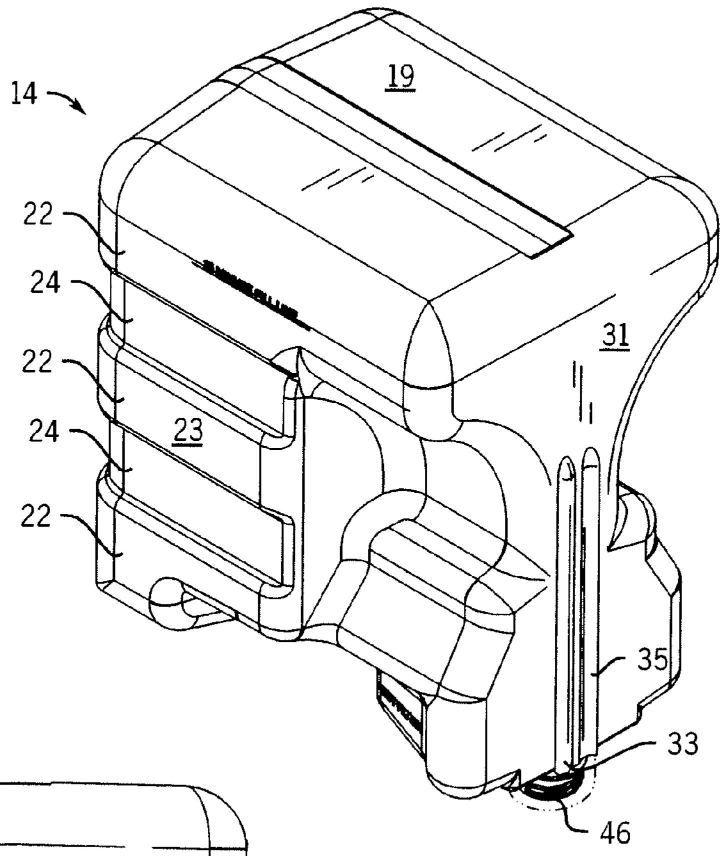
FIG. 7 is a perspective view of an eyewash fluid tank according to an exemplary embodiment.
Figure 8:
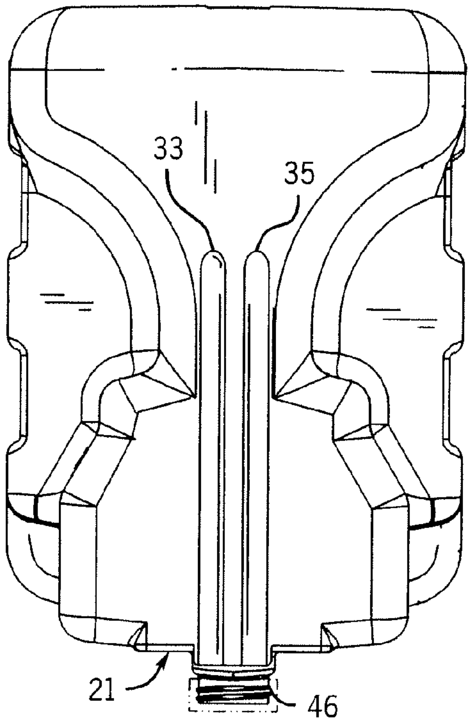
FIG. 8 is an end view of the tank of FIG. 7.
Figure 12:
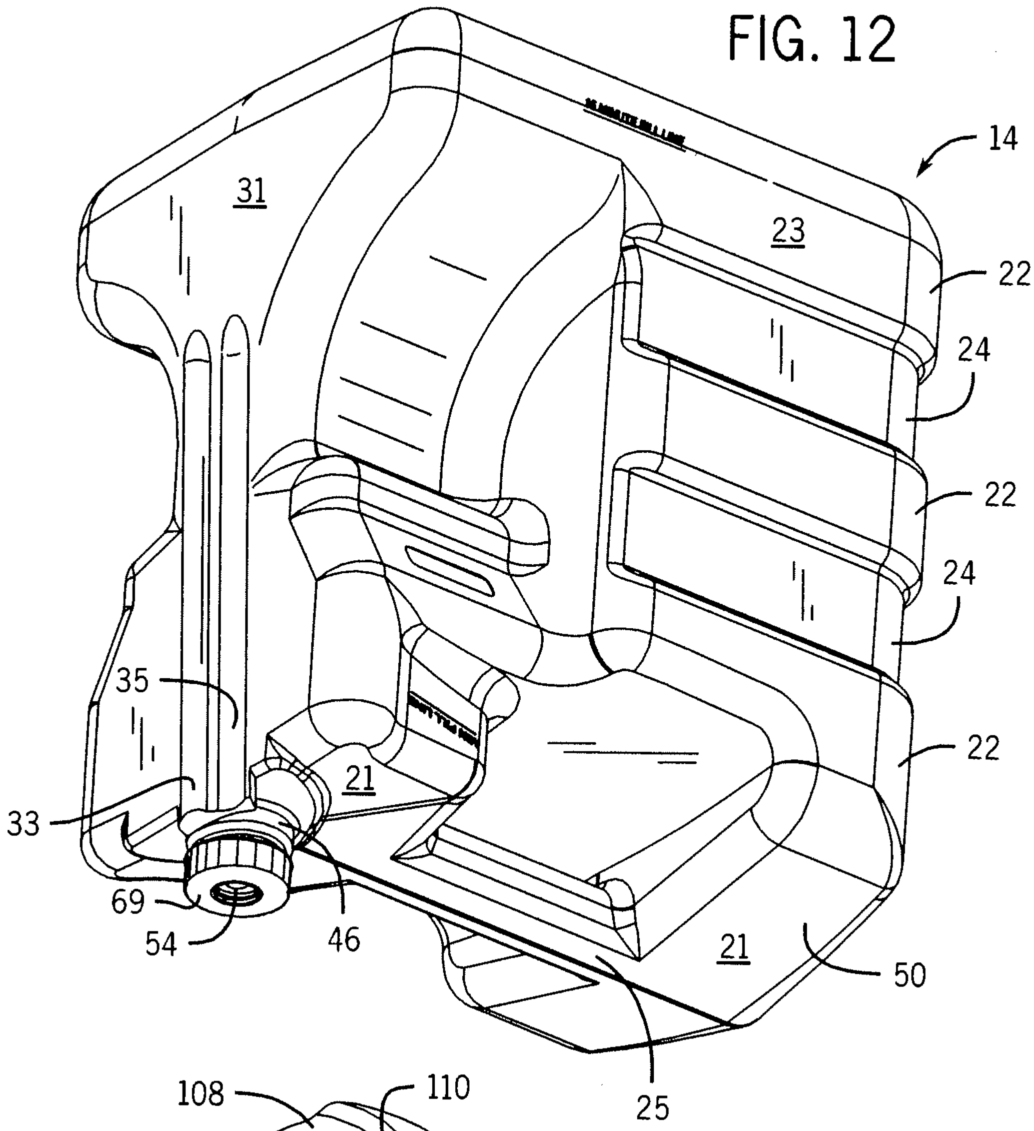
FIG. 12 is a bottom perspective view of an eyewash tank with a check valve and cap coupled to an outlet.
Figure 13:
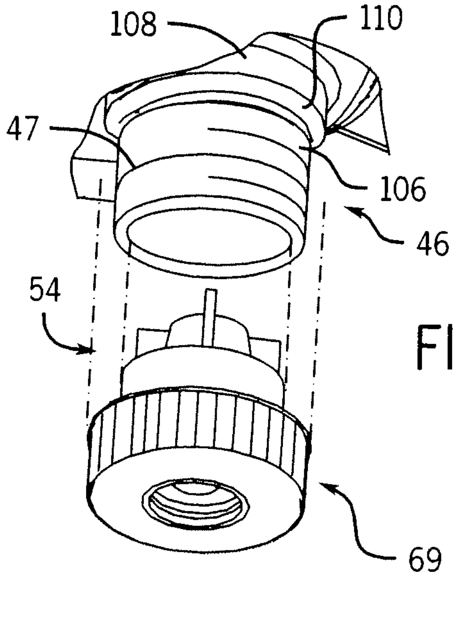
FIG. 13 is a fragmentary exploded view of the tank, check valve, and cap of FIG. 12.
Figure 14:
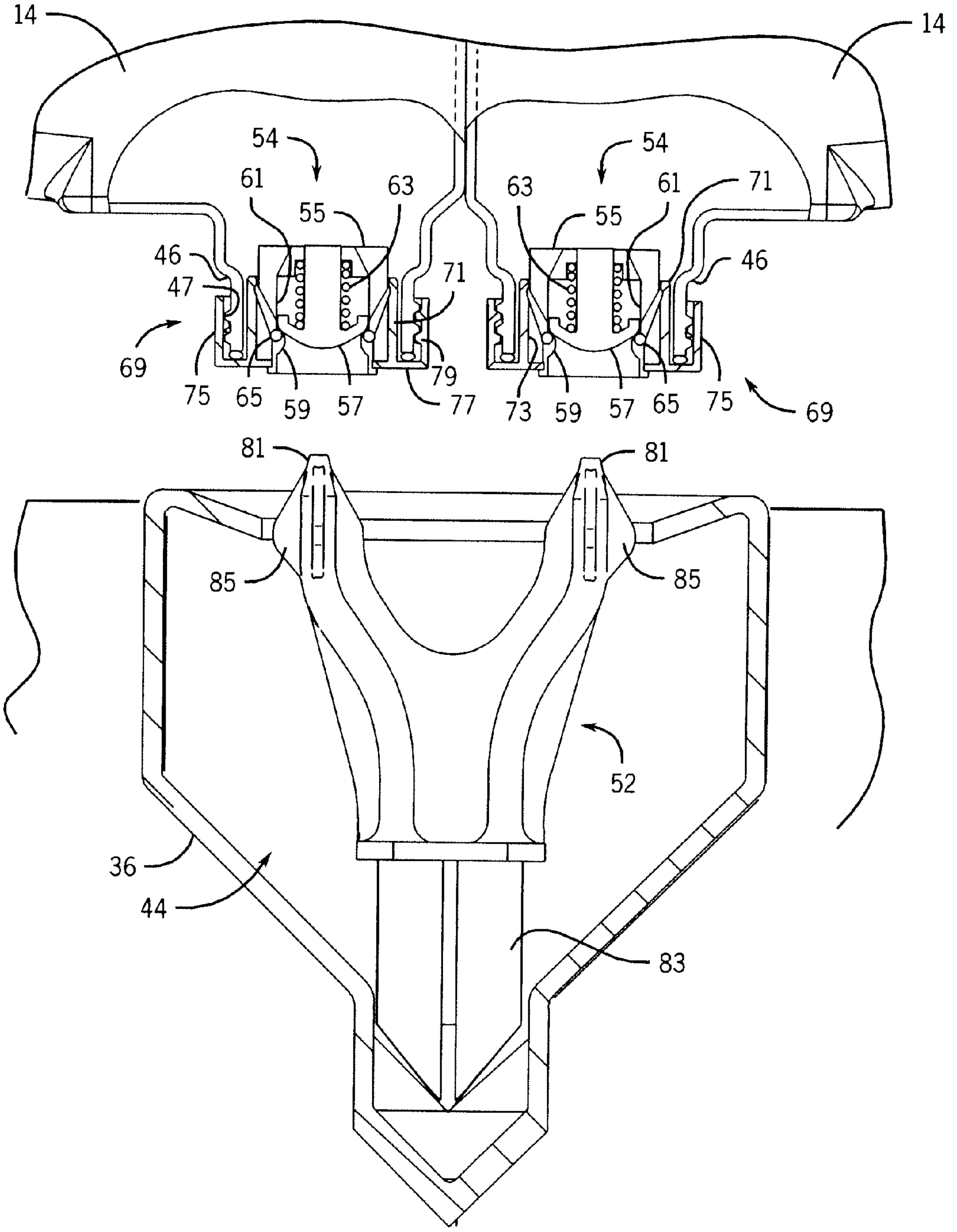
FIG. 14 is a fragmentary exploded section view of the eyewash system of FIG. 1.

FIGS. 1 and 2 show a portable eyewash station or system 10 according to a preferred embodiment. Eyewash system 10 includes a pair of elevated tanks 14 and a dispensing assembly 11. Dispensing assembly 11 includes a base (shown as a pedestal 12) and a dispensing arm 34. Tanks 14 are mounted on pedestal 12 and are configured to deliver a fluid 38 to a user through dispensing arm 34.

According to an exemplary embodiment, tanks 14 rest upon pedestal 12 and are in (flow) communication with an outlet portion of dispensing assembly 11. As shown in FIGS. 1-9, tanks 14 may be removed (e.g., selectively, separately, individually, etc.) from pedestal 12 for refilling, cleaning, replacement, maintenance, inspection, or the like. The use of two (or more) tanks 14 is intended to split or reduce the weight and effort needed by a worker to lift, install or refill the tanks 14 (i.e., rather than a single, larger capacity tank). Using (mating) identical tanks 14 is intended to reduce tooling, manufacturing, and inventory costs. Alternatively, more than two tanks may be used to further reduce the weight needed to be lifted at a time.

Each tank 14 includes a body having a top 19, a bottom 21, a front 23, a rear 27, an outer side 29 and an inner side 31. Ribs 22 and depressions 24 are formed in and disposed along front 23, rear 27, and outer side 29. According to a preferred embodiment, eyewash system 10 uses two identical tanks 14 (e.g., two tanks molded from the same tooling or substantially similar tooling). Tanks 14 are arranged and orientated on pedestal 12 so that inner sides 31 are facing adjacent each other. Inner sides 31 include a rib 33 and a groove 35 spaced apart from a centerline of tank 14 so that rib 33 of a first tank 14 engages groove 35 of an adjacent second tank 14 and rib 33 of the second tank engages groove 35 of the first tank when mounted on pedestal 12. Tank 14 also includes an outlet 46 and handle 25 that are located on bottom 21. Handle 25 is generally centered on bottom 21 so that weight of fluid is evenly distributed when tank 14 is being carried or manipulated by handle 25. Ribs 22, depressions 24, and handle 25 may be easily grasped, carried, or otherwise handled by a worker.

Referring to FIGS. 12-15, outlet 46 of each tank 14 includes a check valve 54. Check valves 54 are configurable between a first (or closed) position and a second (or open) position. Check valves 54 are orientated in openings (e.g., apertures, spouts, etc.) of tanks 14 to inhibit or prevent water from flowing out of tanks 14 when in the closed position. Check valve 54 includes a housing 55, a valve member 57 movable to engage a seat 59 on housing 55, a guide member 61 configured to guide movement of valve member 57, and a spring 63 configured to bias valve member 57 into engagement with seat 59. A sealing member 65 (shown as an o-ring) may be provided to provide a seal between valve member 57 and seat 59. Check valves 54 are coupled to outlets of tanks 14 by caps 69. According to a particularly preferred embodiment, check valve 54 is model number NV25 check valve insert commercially available from Neoperl, Inc. of Waterbury, Conn.

Caps 69 include an annular inner wall 71 defining a bore 73, an annular outer wall 75 generally parallel to inner wall 71 and coupled to inner wall 71 by an intermediate wall 77. Inner wall 71, outer wall 73, and intermediate wall 77 define an annular space for receiving a portion of tank 14 (shown as outlet 46). Outer wall 75 includes a projection providing threads 79 to threadably engage corresponding threads 47 on outlets 46 on tanks 14. Housing 55 of check valve 54 is coupled to cap 69, preferably in a snap fit or interference engagement. Alternatively, the check valve and the cap may be coupled by other techniques (e.g., adhesive, heat-staking, threads, fasteners, etc.) or be integrally formed as a single component. Check valve 54 is held or clamped by cap 69 at tank outlet 46 when cap 69 is threaded onto tank outlet 46 to form a fluid-tight closure. Fluid 38 will not flow from tank outlet 46 until check valve 54 has been opened, even when tanks 14 are inverted prior to installation. Tanks 14 can be removed from eyewash system 10 (e.g. when empty), emptied and cleaned, refilled, in a sealed condition by check valve 54. Tanks 14 may then be reinstalled to eyewash system 10, or kept in storage for later use or as a replacement.

Referring to FIGS. 3, 4, 14, and 15, dispensing assembly 11 provides an inlet portion (shown as a constant level reservoir 36 on pedestal 12) and an outlet portion (shown as flow outlet 42 and spray heads 66 of dispensing arm 34). Reservoir 36 receives fluid 38 from tanks 14, and is connected by a conduit 40 (e.g., a length of flexible hose or tubing) to dispensing arm 34. Reservoir 36 may be constructed (e.g., molded) integral with pedestal 12, or may be molded or fabricated separately and assembled to pedestal 12 by use of interlocking tabs and slots or bumps and depressions, fasteners, adhesive, thermal or solvent welding, etc. Dispensing arm 34 receives fluid 38 from conduit 40 and dispenses fluid 38 upon a user's eyes in a fluid spray 39 (shown in FIGS. 15 and 7).

Reservoir 36 includes a receptacle 44 configured as a generally cylindrically shaped opening in reservoir 36. Outlet 46 of each tank 14 is shown configured as a generally cylindrically shaped projection for engaging or fitting within receptacle 44 so that tanks 14 are engaged with pedestal 12. According to an exemplary embodiment, a check valve may be provided to receptacle 44 so that A check valve activator 52 is coupled to pedestal 12. Activator 52 includes a pair of engagement members 81 disposed upwardly for engaging and opening check valves 54 (shown in FIGS. 3, 10, 11, 14, and 15) that cover outlets 46 of tanks 14. Fluid 38 within tanks 14 is thus prevented from escaping and kept isolated from a dirty or dusty environment during installation of tanks 14 to pedestal 12 until the last moment of engagement with reservoir 36. According to a preferred embodiment, activator 52 is an integrally formed (e.g., molded, cast, fabricated, etc.) "Y"-shaped article (e.g., forked member) where check valve engagement members 81 extend in a generally opposite direction to a mounting member 83. Mounting member 83 engages receptacle 44 to secure activator 52 in place. Each engagement member 81 includes a plurality of guide members or projections 85 (e.g., shown as angled ribs) configured to guide the engagement of engagement members 81 with check valves 54. Activator 52 may be secured to reservoir 36 by use of fasteners, adhesives, solvent or thermal welding, etc., or may be molded or fabricated integral with reservoir 36.

Referring to FIGS. 1-4, pedestal 12 is shown as an integrally molded unit, but can also be assembled of separate molded or fabricated base and tank support portions. Pedestal 12 includes a generally horizontally disposed lower portion 16 which is provided a lower surface (shown as projecting feet 18 in FIG. 4) by which eyewash system 10 may be placed upon a flat surface such as a cart, table top, shelf, pickup truck bed, etc. Lower portion 16 includes a basin 30 having a fluid drain 32.

Dispensing arm 34 is pivotally mounted to pedestal 12 so that it can be pivoted between an upper storage (or stowed) position as shown in FIG. 1 and a lower (deployed or operating) position within basin 30 as shown in FIG. 2. A cover 60 is shown assembled to dispensing arm 34 with screws 62 and provides a surface for application of indicia (e.g., word(s), symbol(s), or other marking(s)) such as manufacturer's identification plate, instructions regarding use and/or maintenance, etc.

FIGS. 3, 13, 14, and 15 show tanks 14 being installed upon pedestal 12. Fluid 38 (shown in FIG. 15) is retained within tanks 14 by check valves 54, which cover tank outlets 46 and prevent fluid from flowing out of tanks 14. Lowering tanks 14 further upon pedestal 12 will allow engagement members 81 of activator 52 to engage check valves 54, whereupon valve member 57 is configured (or moved/pushed) out of engagement with seat 59 on check valve housing 55 so that fluid 38 will flow by gravity out of tank 14, through check valve 54, into reservoir 36 of pedestal 12 through receptacle 44 within rim 90 located at or near the top of reservoir 36. Receptacle 44 within rim 90 has a first diameter configured to receive the outer diameter on tanks 14 and caps 69. Engagement members 81 each include one or more projections 85 (four shown) configured to guide engagement members 81 into engagement with check valves 54. Projections 85 are shown as angled or ramped members. Projections 85 therefore allow a quick, easy, and approximate centering of tank outlet 46 with respect to inlet stage 104 within receptacle 44 during installation of tanks 14, while second stage 108 of tank outlet 46 and projections 85 provide a more accurate centering of tank outlet 46 with respect to inlet stage 104 within receptacle 44 during the final portion of installation. A step 110 between first stage 106 and second stage 108 is provided a lead-in chamfer or radius, as shown, to facilitate transition from first stage 106 engagement to second stage 108 engagement with inlet stage 104. Rim 90 and the outer perimeter formed by projections 85 are conically sloped as shown to facilitate entry of first stage 106 into inlet stage 104. Second stage 108 diameter is made slightly smaller than is the diameter of inlet stage 104, to provide a small air gap for venting of reservoir 36 and, when fluid level within reservoir 36 is below reservoir fluid level 88 (shown in FIG. 15), of tanks 14.

Figure 15:
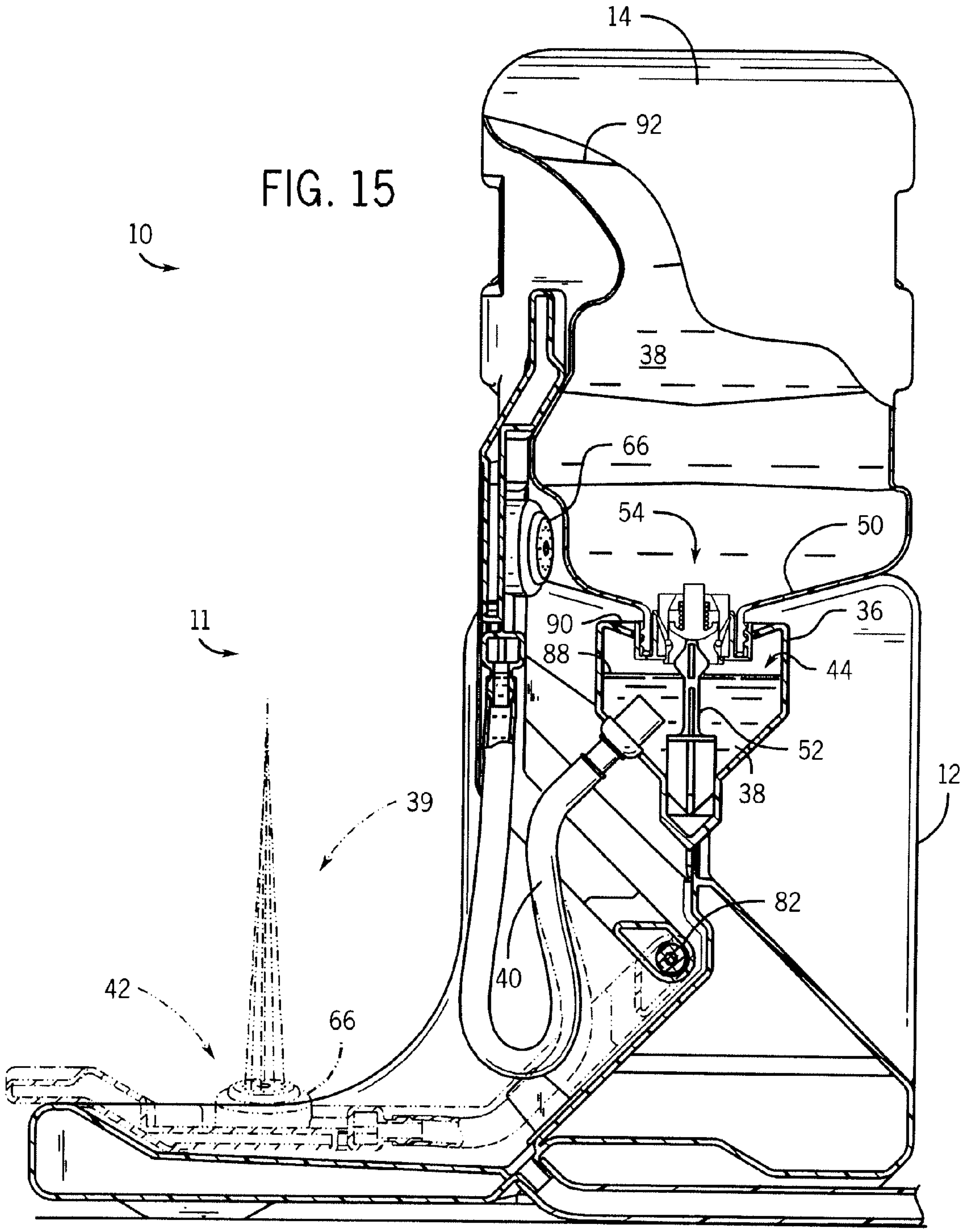
FIG. 15 is a section view of the eyewash system of FIG. 2.

FIG. 15 is a horizontal sectional elevation view of eyewash system 10 showing dispensing arm 34 upwardly disposed in its stowed position. Tanks 14, filled with fluid 38, have been installed on pedestal 12, and engagement members 81 of activator 52 have engaged check valves 54 (which covered and sealed tank outlets 46) to configure check valves 54 into an open condition or position. Fluid 38 fills reservoir 36 from tanks 14 to a reservoir fluid level 88 which is substantially at the elevation of tank outlet 46, and air has been free to "bubble" upwardly through tank outlet 46 to a tank fluid level 92. When the level of fluid 38 within reservoir 36 reaches reservoir fluid level 88, tank outlet 46 is sealed by fluid 38 against entry of air into tanks 14, which prevents flow of fluid 38 out of tanks 14 into reservoir 36. Reservoir 36 is a constant level reservoir; fluid 38 will flow out of tanks 14 into reservoir 36 only to maintain the level of fluid 38 within reservoir 36 to reservoir fluid level 88. Between intermittent uses of eyewash system 10, dispensing arm 34 remains in its stowed position, flow outlet 42 is above reservoir fluid level 88, and no fluid 38 may flow through conduit 40. A rim 90 forming receptacle 44 inhibits air circulation upon the surface of fluid 38 within reservoir 36 sufficiently to preclude a significant rate of evaporation of fluid 38. According to an exemplary embodiment, a gasket (e.g., rubber, butyl, compressible foam, etc.) is provided between rim 90 and tanks 14. With dispensing arm 34 in its stowed position, reservoir 36 will retain reservoir fluid level 88, and tanks 14 will retain tank fluid level 92.

FIG. 15 is a horizontal sectional elevation view of eyewash system 10 showing dispensing arm 34 in its operating position within basin 30. Flow outlet 42 is now lower in elevation than is reservoir fluid level 88, allowing fluid 38 to flow (by gravity) from reservoir 36 through conduit 40 to flow outlet 42 within dispensing arm 34; fluid 38 sprays upwardly through spray heads 66 as a fluid spray 39. Spent fluid spray 39 then falls back into dispensing arm 34, from which it is collected by basin 30 and may be drained by gravity through fluid drain 32. Flowing of fluid 38 from reservoir 36 at least partially empties reservoir 36, lowering the level of fluid 38 within reservoir 36 below reservoir fluid level 88 and below tank outlet 46 (shown in FIG. 15). Air enters tank outlet 46 and "bubbles" upwardly to tank level 92; fluid 38 flows downwardly from tanks 14 into reservoir 36 to maintain reservoir fluid level 88 which provides a substantially continuous flow rate through conduit 40 until dispensing arm 34 is raised or tanks 14 are emptied.

Referring to FIGS. 1-4 and 12, pedestal 12 also includes a generally vertically disposed tank support portion 26 for supporting tanks 14 in the elevated position. Tank support portion 26 has an upper surface with a retaining profile 28 which coacts with a corresponding (v-shaped) retaining profile 50 of a lower surface of tanks 14. Retaining profile 28 may have a V-shape (as shown) or have another shape that resists sliding of one body upon another. Tanks 14 may be secured to pedestal 12 by one or more retaining members and/or combination of retaining members to secure tanks 14 to pedestal 12 along with retaining profile 28. According to an exemplary embodiment shown in FIGS. 4 and 5, the retaining member may also comprise two or more spring biased clips 37 (e.g., spring metal) that engages sides (e.g., front 23, rear 27, outer side 31) of tanks 14. According to an exemplary embodiment shown in FIGS. 1, 2, and 4, the retaining member may comprise two or more straps/webs or spring biased clips 43 (e.g., spring metal) that extend through the opening formed by handle 25. According to an exemplary embodiment shown in FIG. 2, the retaining member 37 may comprise a flexible strap 45 such as nylon webbing stretched across, and residing in recessed in, top 19 of tanks 14.

Lower portion 16 includes basin 30, which provides a fluid drain 32 for collecting fluid spray 39 after discharge and draining it to a suitable receptacle (e.g., a pail). Spent fluid spray 39 is thereby kept from wetting the floor under a user's feet and making it slippery, and is also retained for recovery of contact lenses and for subsequent chemical analysis, if needed to identify the contaminant that was rinsed from the user's eyes.

Dispensing arm 34 is retained in its upwardly disposed stowed position by a detent notch 56 on dispensing arm 34 and a detent boss 58 on pedestal 12 (or alternatively by any suitable method known to those skilled in the art). Dispensing arm 34 may be fabricated with an internal passage for distributing fluid 38 to flow outlet 42. Dispensing arm 34 may be provided as an integral unit (e.g., by injection molding) or may be assembled as shown of a molded portion and a cover 60, in which event cover 60 can be sealed to the molded portion by a gasket or a sealant and secured with fasteners (e.g., self-tapping screws 62). Dispensing arm 34 includes flow outlet 42, through which fluid 38 may spray upon a user's eyes in a fluid spray 39. Flow outlet 42 includes a pair of openings 64 in dispensing arm 34, each opening 64 provided with an associated spray head 66, a seal 68 (e.g., an O-ring), a filter 70, a threaded member 72, and a fastener (e.g., a fastener 98). Threaded member 72 includes three radially projecting arms 74 configured to bear upon the inner rim of each opening 64 within dispensing arm 34 and a threaded central aperture, so that it functions as a nut to engage fastener 98 which secures spray head 66, seal 68, and filter 70 to dispensing arm 34. According to alternative embodiments, one or more spray heads may be molded, or otherwise constructed, integral with dispensing arm 34.

Dispensing arm 34 also includes a first tube stub 76 open to a passage (not shown) within dispensing arm 34 and configured to engage a first end of conduit 40. A second end of conduit 40 is engaged to a second tube stub, shown as a barbed hose coupler 80, which is secured to reservoir 36 at an opening 48 through a wall of reservoir 36, in the illustrated instance by a rubber grommet 78 which is configured to have a tight fit to both the outside of barbed hose coupler 80 and the inside of opening 48. Grommet 78 thereby both frictionally secures and seals barbed hose coupler 80 to reservoir 36. Dispensing arm 34 further includes two pivot pins 82 which engage pivot apertures 84 located within surfaces of pedestal 12 and allow dispensing arm 34 to be pivoted with respect to pedestal 12. A valve (shown as a pinch valve 86 in FIG. 3) is affixed to pedestal 12 by two fasteners (e.g., self-tapping screws 62). Valve 86 (co acting with conduit 40) is configurable between an open position or condition and a closed position or condition.

Conduit 40 engages a valve, shown as pinch valve 86, for shutting off, or preventing, flow of fluid 38 through conduit 40 when dispensing arm 34 is in an operating position but flow of fluid 38 through flow outlet 42 is not desired (e.g., while a worker is performing a maintenance or cleaning task). Valve 86 includes a base portion 116 for mounting of valve 86 upon a surface of pedestal 12, and two projections 118 which are affixed to base portion 116 with a gap between them. The width of the gap between projections 118 is dimensionally slightly less than is twice the wall thickness of the flexible tube or hose used for conduit 40, so that a worker maintaining eyewash system 10 with dispensing arm 34 disposed in its operating position can prevent unwanted flow to and through flow outlet 42 by grasping conduit 40 and manually inserting it into the gap between projections 118 of valve 86, thereby pinching conduit 40 shut in a “disabled” (or “closed” or “off”) configuration. Upon return of dispensing arm 34 back up into its stowed position, conduit 40 is pulled out of engagement with valve 86 and thereby automatically resets to an “enabled” position; when dispensing arm 34 is again lowered to an operating position fluid 38 will flow through conduit 40. The length of conduit 40 and the position of valve 86 is selected to be long enough so that a portion of it will reach and be engageable with valve 86; valve 86 must be located upon a surface of eyewash system 10 which does not move with a pivoting of dispensing arm 34 (e.g., pedestal 12) and which is far enough from pivot 82 for conduit 40 to be certain to be disengaged from valve 86 upon pivoting of dispensing arm 34 to its stowed position.

Figure 16:
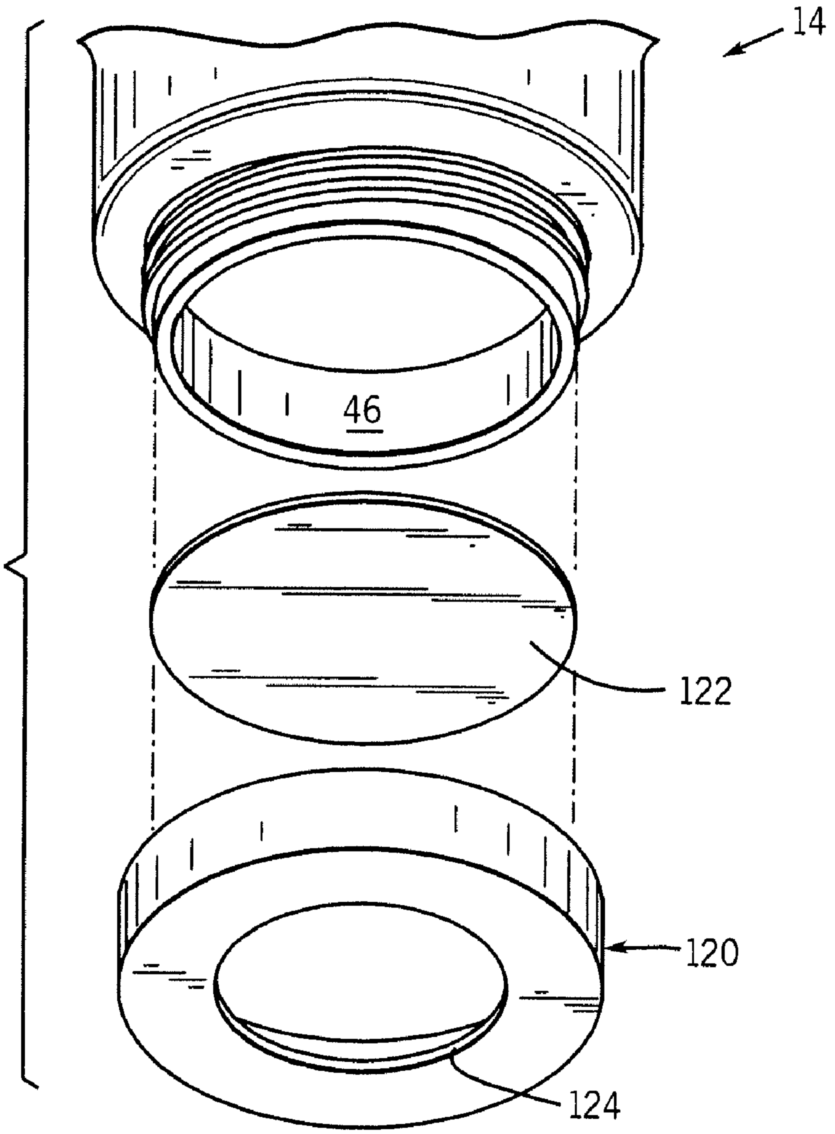
FIG. 16 is an exploded view of the tank, a gasket, and a lid according to an alternative embodiment.

According to an alternative embodiment shown in FIG. 16, tanks 14 are sealed by a lid 120 with a gasket 122 that covers an opening 124 in lid 120, such as shown in U.S. Pat. No. 6,296,626 which is hereby incorporated herein by reference. When tanks 14 are installed on the pedestal, a projection pierces gasket 122. Tanks 14 may thus be removed and reused in a procedure wherein lid 120 is removed, the pierced or ruptured gasket 122 (or seal) is removed, tank 14 is refilled with fluid (e.g. after cleaning), a new gasket 122 (or seal) is installed and secured by lid 120, to be pierced or ruptured by the activator when tank 14 is installed on pedestal 12. The gasket 122 will serve to prevent or substantially reduce fluid spillage when tank 14 is inverted for installation. Gasket 122 may include a foil material, a plastic material, an elastomeric material, or any other type of material known by those who may review this disclosure for such purposes.

It is important to note that the term “check valve” and “activator” are intended to be broad terms and not terms of limitation. For purposes of this disclosure, the term “coupled” shall mean the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may also relate to mechanical, fluid, or electrical relationship between the two components.

It is also important to note that the construction and arrangement of the elements of the eyewash station as shown in the preferred and other exemplary embodiments are illustrative only. Although only a few embodiments of the present invention have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the claims. For example, the basin need not be associated with the pedestal but may instead be affixed to, or a portion of, the dispensing arm. Spray heads may be provided protective caps (e.g., snap-on) which may be associated with the pedestal and automatically disengage the spray heads when the dispensing arm is lowered. The reservoir inlet stage may be a tight fit to the tank second outlet stage, and an air vent, which may include a filter, added to the reservoir. Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and/or omissions may be made in the design, operating conditions and arrangement of the preferred and other exemplary embodiments without departing from the spirit of the present invention as expressed in the appended claims.

What is claimed is:

1. An eyewash system for dispensing an eyewash fluid, the system comprising:

a dispensing assembly having a single inlet portion, an outlet portion, and a valve configurable between an open position and a closed position;

a first tank in communication with the single inlet portion of the dispensing assembly;

a second tank in communication with the single inlet portion of the dispensing assembly;

wherein the outlet portion is configured to dispense eyewash fluid from both the first tank and the second tank when the valve is configured in the open position;

a first check valve coupled to the opening of the first tank and dimensioned and configured to have an open position where fluid is permitted to flow through the first check valve and a closed position where fluid is inhibited from flowing through the first check valve;

a second check valve coupled to the opening of the second tank and dimensioned and configured to have an open position where fluid is permitted to flow through the second check valve and a closed position where fluid is inhibited from flowing through the second check valve; and a single activator having a first member that engages the first check valve to change the first check valve from the closed position to the open position when the first member is inserted into the first check valve, and a second member that engages the second check valve to change the second check valve from the closed position to the open position when the second member is inserted into the second check valve.

2. The system of claim 1 wherein the first tank and the second tank each comprises an integrally formed handle.

3. The system of claim 2 wherein the first tank and the second tank each comprises an opening located adjacent the handle.

4. The system of claim 1 wherein the outlet portion of the dispensing assembly is configured to dispense eyewash fluid from both the first tank and the second tank simultaneously when the valve of the dispensing assembly is configured in the open position.

5. The system of claim 1 wherein the dispensing assembly comprises a base configured to support the first tank and the second tank.

6. The system of claim 5 further comprising a retaining member configured to couple the first tank to the base and the second tank to the base.

7. The system of claim 6 wherein the retaining member comprises a flexible strap.

8. The system of claim 6 wherein the retaining member includes two or more spring biased clips.

9. The system of claim 1 wherein the first member and the second member of the activator are integrally formed with one another.

10. The system of claim 9 wherein the activator is "Y"-shaped.

11. The system of claim 1 wherein the first member and the second member each comprise one or more projections configured to guide the first member into engagement with the first check valve and the second member into engagement with the second check valve.

12. The system of claim 1 further comprising a first cap configured to couple the first check valve to the first tank and a second cap configured to couple the second check valve to the second tank, wherein the first cap and the second cap each comprise an inner wall defining a bore and an outer wall defining an annular space for receiving a portion of the tank.

13. The system of claim 12 wherein the first check valve and the second check valve each comprise a housing, a valve member movable to engage a seat on the housing, a guide member configured to guide movement of the valve member, and a spring configured to bias the valve member into engagement with the seat.

14. The system of claim 12 wherein the outer wall of each of the first and second caps comprises threads extending therefrom and configured to threadably engage the portion of the tank.

15. The system of claim 13 wherein each of the first and second check valves couples to the cap by snap fit engagement between the housing and the bore of the cap.

16. The system of claim 1 wherein the first tank is identical to the second tank.

17. The system of claim 1 wherein the single inlet portion of the dispensing assembly comprises a reservoir to receive the eyewash fluid from the first tank and the second tank and the activator is at least partially located in the reservoir.

18. The system of claim 1 further comprising a conduit, wherein the outlet portion of the dispensing assembly includes at least two flow outlets, and further wherein the conduit provides fluid communication between the single inlet portion of the dispensing assembly and the at least two flow outlets.

* * * * *